(12) United States Patent
Kiani

(10) Patent No.: US 8,401,602 B2
(45) Date of Patent: Mar. 19, 2013

(54) SECONDARY-EMITTER SENSOR POSITION INDICATOR

(75) Inventor: Massi Joe E. Kiani, Laguna Niguel, CA (US)

(73) Assignee: Masimo Corporation, Irvine, CA (US)

(*) Notice: Subject to any disclaimer, the term of this patent is extended or adjusted under 35 U.S.C. 154(b) by 735 days.

(21) Appl. No.: 12/577,667

(22) Filed: Oct. 12, 2009

(65) Prior Publication Data

US 2010/0094106 A1   Apr. 15, 2010

Related U.S. Application Data

(60) Provisional application No. 61/104,890, filed on Oct. 13, 2008.

(51) Int. Cl.
*A61B 5/00* (2006.01)
(52) U.S. Cl. ....................................................... 600/310
(58) Field of Classification Search ................... 600/310
See application file for complete search history.

(56) References Cited

U.S. PATENT DOCUMENTS

| | | | |
|---|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,278,627 A | 1/1994 | Aoyagi et al. |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |

(Continued)

*Primary Examiner* — Rodney Fuller
(74) *Attorney, Agent, or Firm* — Knobbe Martens Olson & Bear LLP

(57) ABSTRACT

A secondary-emitter sensor position indicator has primary emitters that transmit light having primary wavelengths and at least one secondary emitter that transmits light having at least one secondary wavelength. A detector outputs a sensor signal in response to received light. An attachment assembly, in a sensor-on condition, positions the emitters and detector relative to a tissue site so that the sensor signal is substantially responsive to the primary wavelength light after attenuation by pulsatile blood flow within the tissue site and is negligibly responsive to the secondary wavelength light. The attachment assembly, in a sensor out-of-position condition, positions the secondary emitter relative to the tissue site so that the sensor signal is at least partially responsive to the secondary wavelength.

18 Claims, 9 Drawing Sheets

U.S. PATENT DOCUMENTS

| | | | |
|---|---|---|---|
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 * | 2/2003 | Kiani et al. ................ 600/322 |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Diab et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 * | 8/2004 | Kiani et al. ................ 600/323 |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |

| | | | | | | |
|---|---|---|---|---|---|---|
| 7,332,784 B2 | 2/2008 | Mills et al. | 7,489,958 B2 | 2/2009 | Diab et al. | |
| 7,340,287 B2 | 3/2008 | Mason et al. | 7,496,391 B2 | 2/2009 | Diab et al. | |
| 7,341,559 B2 | 3/2008 | Schulz et al. | 7,496,393 B2 | 2/2009 | Diab et al. | |
| 7,343,186 B2 | 3/2008 | Lamego et al. | D587,657 S | 3/2009 | Al-Ali et al. | |
| D566,282 S | 4/2008 | Al-Ali et al. | 7,499,741 B2 | 3/2009 | Diab et al. | |
| 7,355,512 B1 | 4/2008 | Al-Ali | 7,499,835 B2 | 3/2009 | Weber et al. | |
| 7,371,981 B2 | 5/2008 | Abdul-Hafiz | 7,500,950 B2 | 3/2009 | Al-Ali et al. | |
| 7,373,193 B2 | 5/2008 | Al-Ali et al. | 7,509,154 B2 | 3/2009 | Diab et al. | |
| 7,373,194 B2 | 5/2008 | Weber et al. | 7,509,494 B2 | 3/2009 | Al-Ali | |
| 7,376,453 B1 | 5/2008 | Diab et al. | 7,526,328 B2 | 4/2009 | Diab et al. | |
| 7,377,794 B2 | 5/2008 | Al-Ali et al. | 7,530,942 B1 | 5/2009 | Diab | |
| 7,377,899 B2 | 5/2008 | Weber et al. | 7,530,949 B2 | 5/2009 | Al Ali et al. | |
| 7,383,070 B2 | 6/2008 | Diab et al. | 7,530,955 B2 | 5/2009 | Diab et al. | |
| 7,415,297 B2 | 8/2008 | Al-Ali et al. | 7,563,110 B2 | 7/2009 | Al-Ali et al. | |
| 7,428,432 B2 | 9/2008 | Ali et al. | 7,596,398 B2 | 9/2009 | Al-Ali et al. | |
| 7,438,683 B2 | 10/2008 | Al-Ali et al. | 7,618,375 B2 | 11/2009 | Flaherty | |
| 7,440,787 B2 | 10/2008 | Diab | D606,659 S | 12/2009 | Kiani et al. | |
| 7,454,240 B2 | 11/2008 | Diab et al. | 7,647,083 B2 | 1/2010 | Al-Ali et al. | |
| 7,467,002 B2 | 12/2008 | Weber et al. | D609,193 S | 2/2010 | Al-Ali et al. | |
| 7,469,157 B2 | 12/2008 | Diab et al. | 7,904,130 B2 * | 3/2011 | Raridan, Jr. | 600/323 |
| 7,471,969 B2 | 12/2008 | Diab et al. | 2007/0129616 A1* | 6/2007 | Rantala | 600/323 |
| 7,471,971 B2 | 12/2008 | Diab et al. | 2009/0076354 A1* | 3/2009 | Huiku | 600/331 |
| 7,483,729 B2 | 1/2009 | Al-Ali et al. | | | | |
| 7,483,730 B2 | 1/2009 | Diab et al. | * cited by examiner | | | |

SECONDARY-EMITTER SENSOR POSITION INDICATOR

CROSS-REFERENCE TO RELATED APPLICATIONS

The present application claims priority benefit under 35 U.S.C. §119(e) to U.S. Provisional Patent Application Ser. No. 61/104,890, filed Oct. 13, 2008, titled Secondary-Emitter Sensor Position Indicator, hereby incorporated by reference herein.

BACKGROUND OF THE INVENTION

Pulse oximetry is a technique that utilizes a noninvasive sensor to determine a person's oxygen status. An optical sensor used in pulse oximetry has light emitting diodes (LEDs) that transmit optical radiation of red and infrared wavelengths into a tissue site. A detector in the sensor responds to the intensity of the optical radiation after attenuation by pulsatile arterial blood flowing within the tissue site. Based on this response, a processor determines measurements for $SpO_2$ and pulse rate among other parameters. Pulse oximeters capable of reading through motion induced noise are available from Masimo Corporation ("Masimo") of Irvine, Calif. Moreover, portable and other pulse oximeters capable of reading through motion induced noise are disclosed in at least U.S. Pat. Nos. 6,770,028, 6,658,276, 6,157,850, 6,002,952, and 5,769,785, which are owned by Masimo and are incorporated by reference herein. Corresponding low noise optical sensors are also available from Masimo and are disclosed in at least U.S. Pat. Nos. 6,985,764, 6,813,511, 6,792,300, 6,256,523, 6,088,607, 5,782,757, 5,758,644 and 5,638,818. Such reading through motion pulse oximeters and low noise sensors have gained rapid acceptance in a wide variety of medical applications, including surgical wards, intensive care and neonatal units, general wards, home care, physical training and virtually all types of monitoring scenarios. Moreover, pulse oximeters capable of reading through motion induced noise including Radical®, Rad-5™, Rad-8™, Rad-9™ and PPO+™ monitors and low noise optical sensors including LNOP®, LNCS® and SofTouch™ disposable, reusable, reSposable™ and multisite sensors and cables are also available from Masimo.

Further, noninvasive blood parameter monitors capable of measuring parameters in addition to $SpO_2$, such as HbCO, HbMet and Hbt and corresponding multiple wavelength optical sensors are also available from Masimo. Noninvasive blood parameter monitors and corresponding multiple wavelength optical sensors are described in at least U.S. patent application Ser. No. 11/367,013, filed Mar. 1, 2006, titled Multiple Wavelength Sensor Emitters and U.S. patent application Ser. No. 11/366,208, filed Mar. 1, 2006, titled Noninvasive Multi-Parameter Patient Monitor, both assigned to Masimo Laboratories, Irvine, Calif. (Masimo Labs) and both incorporated by reference herein. Moreover, multiple parameter monitors and multiple wavelength sensors including Radical-7™, Rad57™ and Rad87™ monitors and Rainbow™-brand adhesive and reusable sensors are available from Masimo. MS- and MX-brand processor boards are also available from Masimo.

SUMMARY OF THE INVENTION

Problems arise if a pulse oximeter or other blood parameter monitor is connected to an optical sensor that is not properly positioned on a tissue site or becomes partially or completely dislodged from a patient, a sensor out-of-position condition including sensor-off and sensor mis-position conditions. When an optical sensor is properly positioned on a tissue site, the detector only receives LED emitted light that has propagated via the tissue site to the detector after tissue scattering and absorption. Thus, the AC detector signal that results accurately reflects the differential absorption of constituents in the pulsatile arterial blood. If a sensor is off a tissue site or is mis-positioned on the tissue site, the detector may directly receive LED emitted light, i.e. light that has not propagated through any tissue. Despite a sensor out-of-position condition, a blood parameter monitor may continue to detect an AC signal, which can be induced at the detector by other than pulsatile arterial attenuation of LED emitted light. Small patient movements, vibrations, air flow or other perturbations may cause the pathlength between the LEDs and detector to vary, resulting in an AC detector signal that can be mistakenly interpreted by the monitor as due to pulsatile arterial blood. Further, ambient light may reach the detector, and any modulation of the ambient light due to AC power, power fluctuations, moving objects, such as a fan, among other perturbations can also be mistaken as a pulsatile arterial signal. Sensor out-of-position errors are serious because a blood parameter monitor may still display a normal measurement, potentially leading to critical missed events, such as an oxygen desaturation.

An aspect of a sensor position indicator regards an optical sensor with a sensor-on condition in which the optical sensor is attached to and aligned with a tissue site so as to transmit light into the tissue site and detect the light after attenuation by pulsatile blood flow within the tissue site and a sensor out-of-position condition in which the sensor is unattached to or misaligned with the tissue site. The sensor position indicator comprises an optical sensor having primary emitters and a detector. The primary emitters generate light generally centered around each of multiple primary wavelengths. The primary emitters transmit light into a tissue site in a sensor-on condition. The detector, in the sensor-on condition, outputs a sensor signal responsive to the primary wavelength light after attenuation by pulsatile blood flow within the tissue site. A secondary emitter generates light generally centered around a secondary wavelength. The secondary emitter transmitted light is at least substantially attenuated by the tissue site. The detector, in the sensor-on condition, is at least substantially blocked by the tissue site from the secondary emitter so that the sensor signal is not responsive to the secondary wavelength light. The detector, in a sensor out-of-position condition, is at least partially exposed to the secondary emitter so that the sensor signal is responsive to the secondary wavelength light. A processor is responsive to the sensor signal so as to calculate a blood-related physiological parameter in the sensor-on condition and so as to indicate the sensor is unattached to or misaligned with the tissue site in the sensor out-of-position condition.

In various embodiments, the optical sensor has a sensor mis-positioned condition in which the optical sensor is misaligned with the tissue site. The sensor position indicator further comprises a second secondary emitter that generates light generally centered around the secondary wavelength. The detector, in the sensor mis-positioned condition, is at least substantially blocked from the second secondary emitter by the tissue site and is at least partially exposed to the secondary emitter so that the sensor signal is not responsive to the second secondary emitter and is responsive to the secondary emitter. The processor is responsive to the sensor signal so as to indicate the optical sensor is misaligned with the tissue site in the mis-positioned sensor condition. The optical sensor also has a sensor-off position in which the optical sensor is unattached to or substantially misplaced on the tissue site. The detector, in the sensor-off condition, is at least partially exposed to the secondary emitter and the second secondary emitter so that the sensor signal is responsive to both the secondary emitter and the second secondary emitter. The processor is responsive to the sensor signal so as to indicate that the optical sensor is unattached to or substantially misplaced on the tissue site in the sensor-off condition.

The optical sensor also has a sensor over-positioned condition where the tissue site is over-inserted into the optical sensor. The sensor position indicator further comprises a third secondary emitter that generates light generally centered around the secondary wavelength. The detector, in the sensor-on condition, is at least substantially exposed to the third secondary emitter so that the sensor signal is responsive to the third secondary emitter. The detector, in the sensor over-positioned condition, is at least substantially blocked from the third secondary emitter by the tissue site so that the sensor signal is not responsive to the third secondary emitter. The processor is responsive to the sensor signal so as to indicate the tissue site is over-inserted into the optical sensor in the sensor over-positioned condition. The primary wavelengths may include red and IR and the secondary wavelength may be blue or green. The secondary emitter may be located external to the optical sensor so that the secondary wavelength light is ambient light with respect to the optical sensor. The secondary emitter may be driven asynchronously relative to the primary emitters.

An aspect of an optical sensing method comprises providing an optical sensor having a primary emitter and a detector. The primary emitter is activated with a primary drive signal so as to transmit light having a primary wavelength into a fleshy tissue site. A secondary emitter is activated with a secondary drive signal so as to transmit light having a secondary wavelength proximate the fleshy tissue site. The primary wavelength light is detected after attenuation by pulsatile blood flow within the tissue site. The secondary wavelength light is detected. A physiological parameter is calculated according to detected primary wavelength light. A sensor position of the primary emitter and the detector relative to the fleshy tissue site is determined according to the detection of secondary wavelength light.

In various embodiments, the primary drive signal and the secondary drive signal are synchronized so that on periods of the secondary drive signal occur during off periods of the primary drive signal. Determining sensor position may comprise indicating a sensor-on condition according to undetected secondary wavelength light during an on period of the secondary drive signal and indicating a sensor out-of-position condition according to undetected secondary wavelength light during on periods of the secondary drive signal. A second secondary emitter may be activated with a second secondary drive signal and a sensor-off condition indicated according to the undetected secondary wavelength light during on periods of the secondary drive signal and second secondary drive signal. A sensor mis-position condition may be indicated according to detected secondary wavelength light during on periods of the secondary drive signal and according to undetected secondary wavelength light during on periods of the second secondary drive signal. A third secondary emitter may be activated with a third secondary drive signal and a sensor over-position condition indicated according to detected secondary wavelength light during on periods of the third secondary drive signal.

An aspect of a physiological measurement system comprises an optical sensor having primary emitters, at least one secondary emitter, a detector and an attachment assembly. A physiological monitor is in communications with the optical sensor. The primary emitters transmit light having a primary wavelengths. At least one secondary emitter transmits light having at least one secondary wavelength. The detector outputs a sensor signal in response to received light. The attachment assembly, in a sensor-on condition, positions the emitters and detector relative to a tissue site so that the sensor signal is substantially responsive to the primary wavelength light after attenuation by pulsatile blood flow within the tissue site and is negligibly responsive to the secondary wavelength light. The attachment assembly, in a sensor out-of-position condition, positions at least one secondary emitter relative to the tissue site so that the sensor signal is at least partially responsive to the at least one secondary wavelength.

In various embodiments, a first secondary emitter is located in a first position relative to the primary emitters. A second secondary emitter is located in a second position relative to the primary emitters. The attachment assembly, in a sensor mis-positioned condition, positions the secondary emitters relative to the tissue site so that the sensor signal is negligibly responsive to the first secondary emitter and at least partially responsive to the second secondary emitter. The attachment assembly, in a sensor-off condition, may position the secondary emitters relative to the tissue site so that the sensor signal is at least partially responsive to the first secondary emitter and the second secondary emitter. A third secondary emitter may be located in a third position relative to the primary emitters. The attachment assembly, in a sensor-on condition, positions the secondary emitters relative to the tissue site so that the sensor signal is negligibly responsive to the first and second secondary emitters and at least partially responsive to the third secondary emitter. The attachment assembly, in a sensor over-positioned condition, positions the secondary emitters relative to the tissue site so that the sensor signal is negligibly responsive to the first, second and third secondary emitters. A processor portion of the physiological monitor may operate on the sensor signal so as to determine the position of a finger relative to the sensor according to at least multiple ones of a sensor-on condition, a sensor out-of-position condition, a sensor off condition and a sensor mis-positioned condition. A display portion of the physiological monitor may be responsive to the processor determination of sensor and finger position so as to graphically depict the position of a finger relative to the sensor. An alarm portion of the physiological monitor may be responsive to the processor determination of sensor and finger position so as to audibly indicate the position of a finger relative to the sensor.

DETAILED DESCRIPTION OF THE PREFERRED EMBODIMENTS

Figure 1:
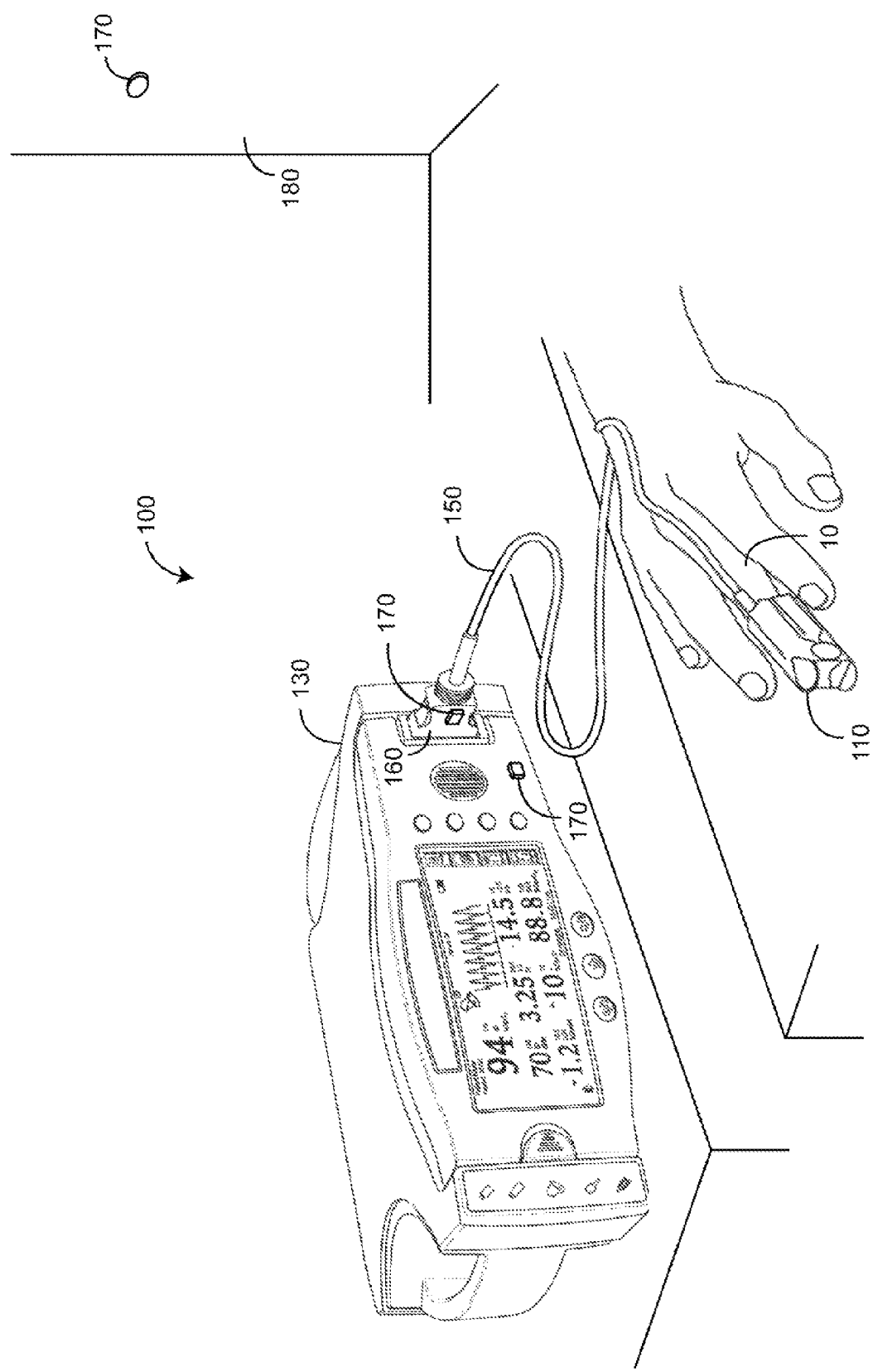
FIG. 1 is a perspective illustration of a physiological measurement system utilizing a sensor position indicator.
Figure 2:
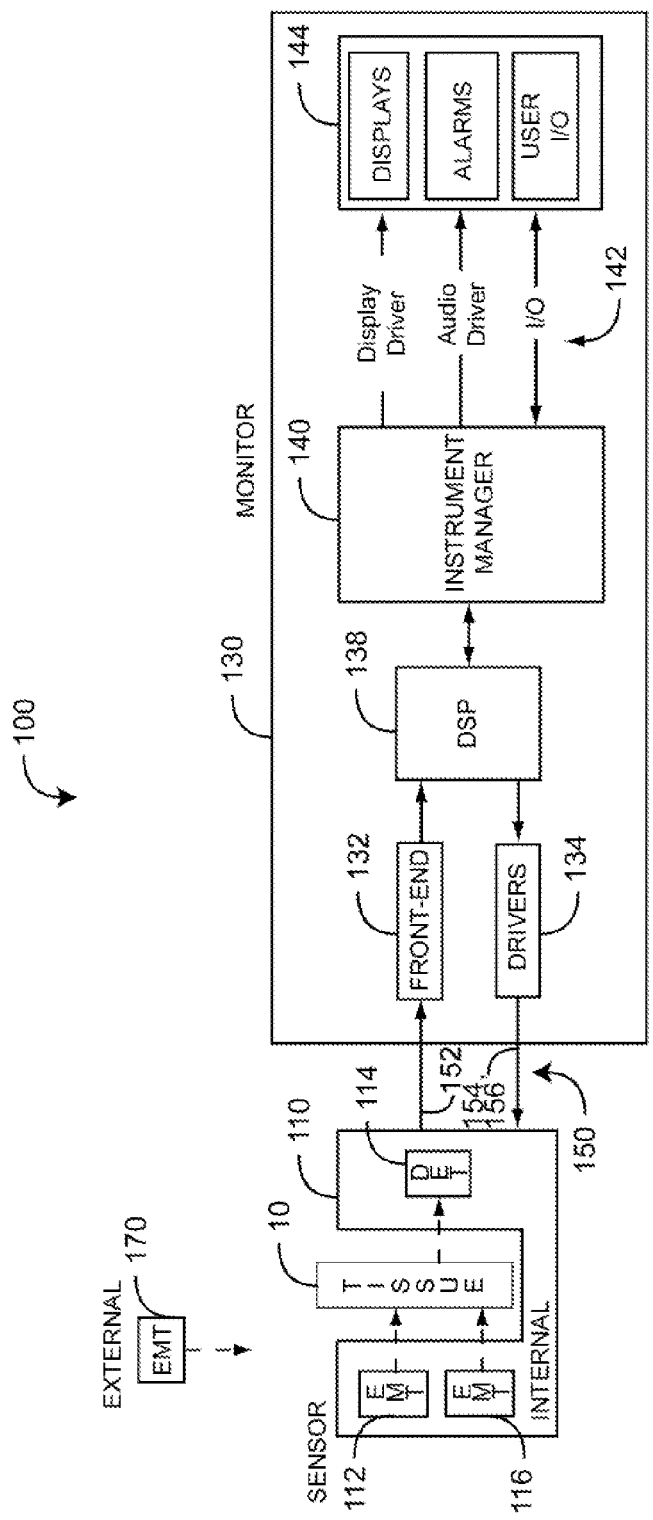
FIG. 2 is a block diagram of a physiological measurement system utilizing a sensor position indicator.

FIGS. 1-2 illustrate a physiological measurement system 100 which measures blood constituents and related parameters, such as oxygen saturation, pulse rate, perfusion index (PI), pleth variability index (PVI™), HbCO, HbMet and Hbt, to name a few. The physiological measurement system 100 includes an optical sensor 110 applied to a tissue site 10, a monitor 130 and a cable 150 that physically and electrically connects the sensor 110 to the monitor 130. Advantageously, the physiological measurement system 100 also utilizes a sensor position indicator responsive to improper placement of the sensor 110 on a finger or other tissue site 10, as described in detail below.

As shown in FIGS. 1-2, the patient monitor 130 communicates with the sensor 110 to receive one or more intensity signals indicative of one or more physiological parameters. Drivers 134 convert digital control signals into analog drive signals 154 capable of driving primary emitters 112 that transmit optical radiation having multiple primary wavelengths. The drivers 134 also provide drive signals 156 capable of driving secondary emitters 116 having one or more secondary wavelengths. A detector 114 responds to the intensity of the optical radiation after attenuation by pulsatile blood flow within the tissue site 10 and generates a corresponding sensor signal 152. A front-end 132 converts the analog sensor signal 152 into digital data input to a digital signal processor (DSP) 138. The DSP 138 comprises any of a wide variety of data and signal processors capable of executing programs for determining physiological parameters from input data. The instrument manager 140 may comprise one or more microcontrollers providing system management, such as monitoring the activity of the DSP 138. The instrument manager 140 also has communications 142 with displays, alarms and user input/output (I/O) 144. In an embodiment, a display 144 depicts the position of a finger relative to the sensor according to any of a sensor on, a sensor out-of-position, a sensor off and a sensor mis-positioned condition.

Also shown in FIGS. 1-2, in an embodiment a sensor position indicator incorporates external secondary emitters 170 located outside of the sensor 110. In an embodiment, a sensor position indicator incorporates internal secondary emitters 116 located inside the sensor 110. The secondary emitters 116, 170 have one or more wavelengths selected to be at least substantially attenuated by tissue. In an embodiment, secondary emitter wavelengths are selected from the blue or green region of the visible spectrum so as to be highly absorbed by water and, hence, substantially attenuated by the substantial water content of tissue. In this manner, the sensor signal 152 responsive to a secondary emitter 116, 170 is indicative of a sensor-off or a sensor mis-positioned condition. That is, for the detector 114 to sense a secondary emitter 116, 170, the detector 114 must be at least partially uncovered by the tissue site 10.

As shown in FIG. 1, external secondary emitters 170 can be placed in one or more locations in or around the measurement system 100. These secondary emitters 170 enable the detection of a sensor-off or sensor mis-positioned condition via generation of ambient light having at least one secondary wavelength. As examples, external secondary emitters 170 can be disposed on the monitor 130, on the cable connector 160, in the surrounding room, such as on a wall 180, or on other instruments in the room (not shown), or combinations of these locations. External secondary emitters 170 may be free running, driven by the monitor in sync with primary emitters or may be driven by another instrument.

As shown in FIG. 2, one or more internal secondary emitters 116 are placed in a sensor proximate a primary emitter 112 and distal a detector 114 used for blood parameter measurements. These secondary emitters 116 enable the detection of a sensor-off or sensor mis-positioned condition via generation of sensor generated light having at least one secondary wavelength. Internal secondary emitters 116 may be free running or driven by the monitor in sync with the primary emitters.

Figure 3A:
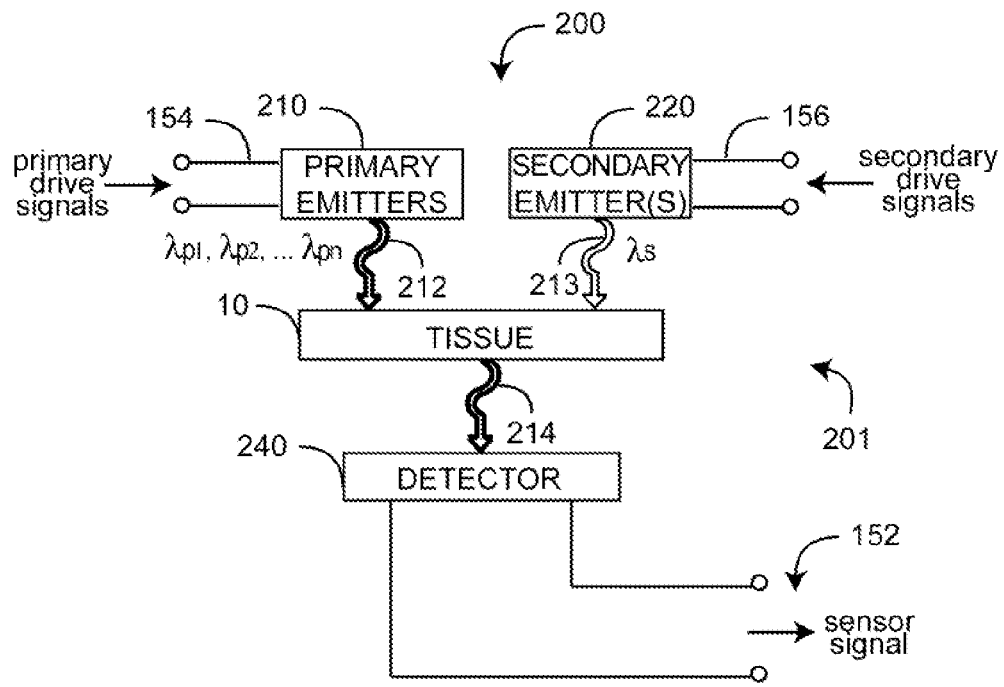
FIGS. 3A-B are general block diagrams of a secondary-emitter sensor position indicator illustrating sensor-on and sensor-off conditions, respectively.
Figure 3B:
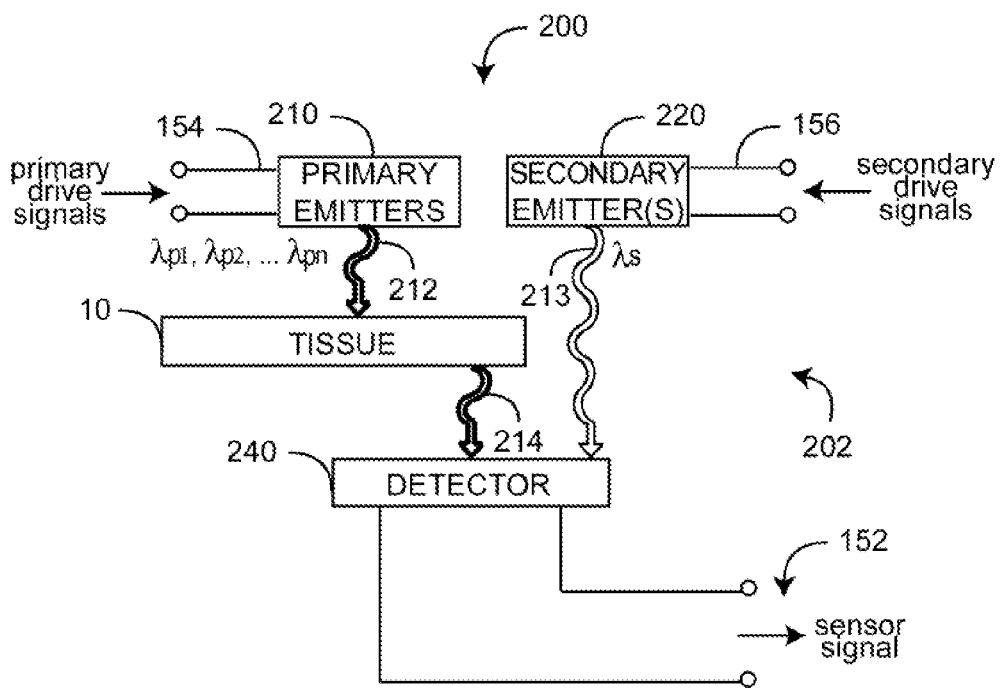

FIGS. 3A-B illustrate a sensor 200 having a secondary emitter configured for sensor position indication. The sensor 200 has primary emitters 210 capable of transmitting light having primary wavelengths ($\lambda p$) 212 into a tissue site 10. A detector 240 is capable of detecting the transmitted light 212 after attenuation by the tissue site 10 and outputting a primary signal 250 responsive to the detected light 214. The primary signal 250 is indicative of at least one physiological parameter corresponding to the tissue site 10. Advantageously, the sensor 200 is associated with at least one secondary emitter 220 having at least one secondary wavelength ($\lambda s$) 213 that is at least substantially attenuated by the tissue site 10. In this manner, the response of the detector signal 250 to the secondary emitter 220 is indicative of sensor position, as described in further detail below.

As shown in FIG. 3A, a sensor-on condition 201 is where the tissue site 10 is properly placed relative to the detector 240 so that accurate physiological measurements can be made. In particular, a primary emitter 210 is placed so as to illuminate a blood-perfused tissue site 10, such as a nail bed, and the detector 240 is positioned so that only light transmitted by the primary emitter 210 and attenuated by pulsatile blood flowing within the tissue site 10 is received by the detector 240. Specifically, in a sensor-on condition 201, the detector 240 is not exposed to ambient light or light transmitted directly from emitter 210 to detector 240 without tissue site attenuation, such as by light-piping or reflection around the tissue site or otherwise. For example, in a sensor-on condition 201, constraints on the placement and relative location of emitter, tissue site and detector result in a sensor signal having a negligible contribution from light having a secondary wavelength $\lambda s$ 213.

As shown in FIG. 3B, a mis-positioned sensor condition or a sensor-off condition 202 is where the tissue site 10 is displaced relative to the detector 240 so that light having a secondary wavelength $\lambda s$ 213 reaches the detector 240, i.e. the detector signal 250 is also responsive to a secondary emitter 220. For example, in a mis-positioned sensor condition or a sensor-off condition 202, a sensor signal could have a substantial contribution from ambient light or other transmitted light that has not reach the detector 240 via tissue site 10 attenuation. Various embodiments of a sensor position indicator utilizing a secondary emitter are described with respect to FIGS. 4-9, below.

Figure 4A:
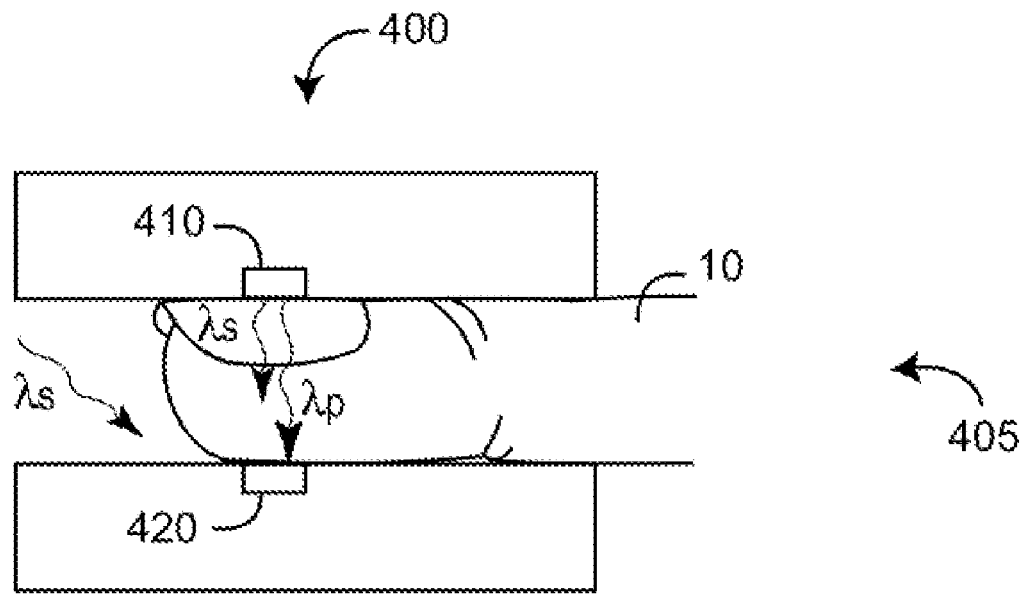
FIGS. 4A-B are side view illustrations of a secondary-emitter sensor position indicator illustrating sensor-on and sensor-off conditions, respectively.
Figure 4B:
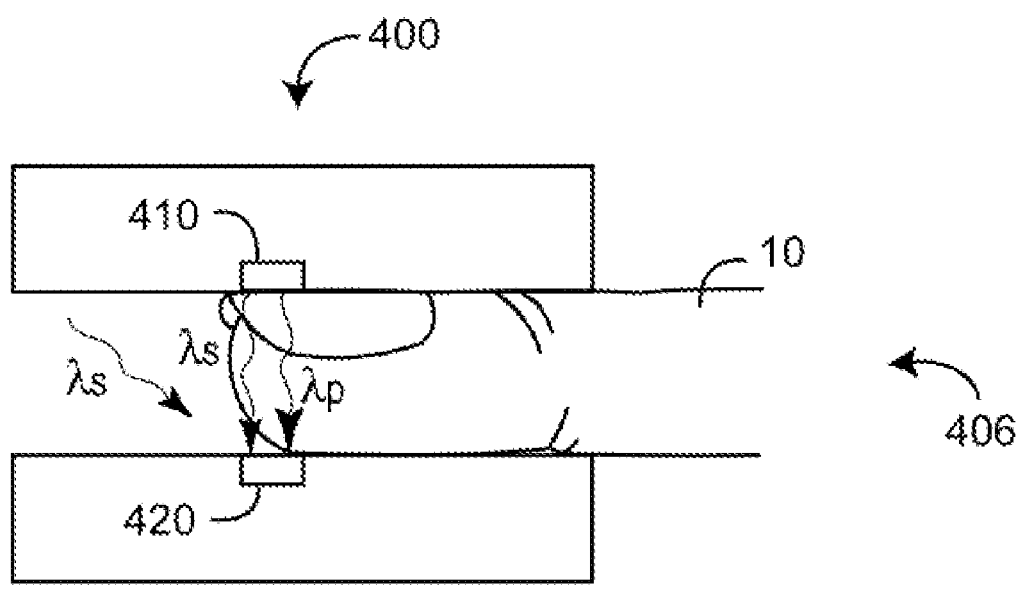

FIGS. 4A-B illustrate a secondary emitter sensor embodiment in a sensor-on condition and a mis-positioned sensor condition, respectively. The sensor 400 has a primary emitter 410 that emits light having multiple primary wavelengths λp into a tissue site 10 and a detector 420 that detects the emitted light after attenuation by the tissue site 10.

As shown in FIG. 4A, in a sensor-on condition 405, the tissue site 10 completely covers the detector 420. As such, light having a secondary wavelength λs is at least substantially attenuated by the tissue site 10 so that the detector 420 is not responsive to a secondary emitter. That is, the failure to detect emission from one or more secondary emitters indicates a sensor-on condition 405.

As shown in FIG. 4B, in a mis-positioned sensor condition 406, the detector 420 is exposed to light having a secondary wavelength λs including light from one or more secondary emitters. That is, the detection of wavelength λs from one or more secondary emitters indicates either a mis-positioned sensor condition 406 or a sensor-off condition (not shown).

As shown in FIGS. 4A-B, one or more external secondary emitters 170 (FIG. 1) or internal secondary emitters 116 (FIG. 2) have at least one secondary wavelength λs that is at least substantially attenuated by the tissue site 10. Accordingly, a sensor position relative to the tissue site 10 is indicated according to whether a secondary wavelength is detected. In an embodiment, internal secondary emitters, if any, are driven synchronously with the primary emitters, as described with respect to FIGS. 5A-B, below. In an embodiment, external secondary emitters, if any, are free-running, i.e. driven asynchronously from the primary emitters, as described with respect to FIG. 5C, below. In an embodiment, a detector response in one or more time slots where no primary emitters are activated indicates a sensor-off condition, as described with respect to FIGS. 5A-C, below. In an embodiment, the emitter 410 is an array of LEDs including LEDs that emit primary wavelengths and LEDs that emit one or more secondary wavelengths. An emitter array is described in U.S. patent application Ser. No. 11/367,013, cited above and incorporated by reference herein.

Figure 5A:
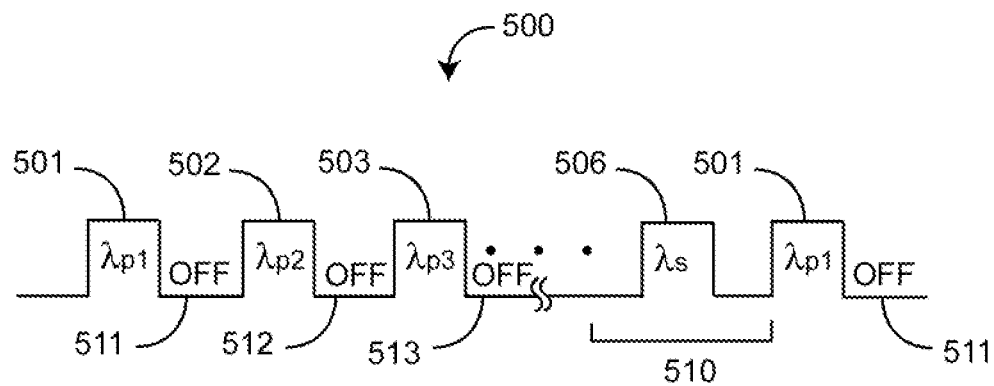
FIGS. 5A-C are timing diagrams for a secondary-emitter sensor position indicator illustrating a primary-emitter drive signal and corresponding detector output signals for a sensor-off condition with synchronous and asynchronous secondary emitters, respectively.
Figure 5B:
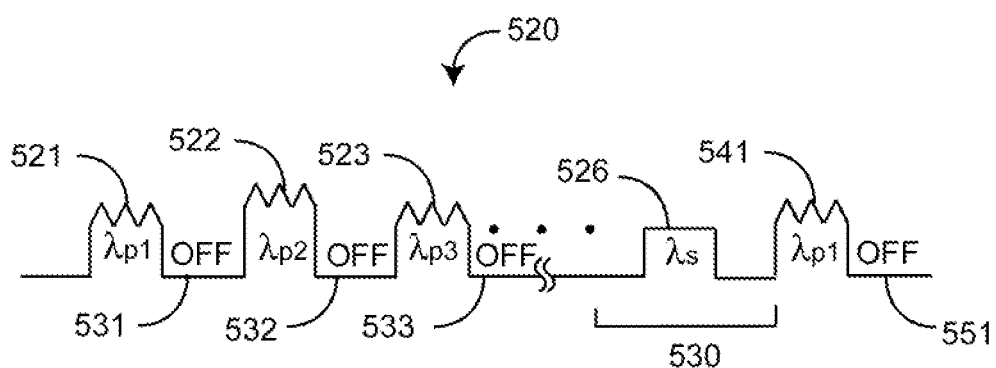
Figure 5C:
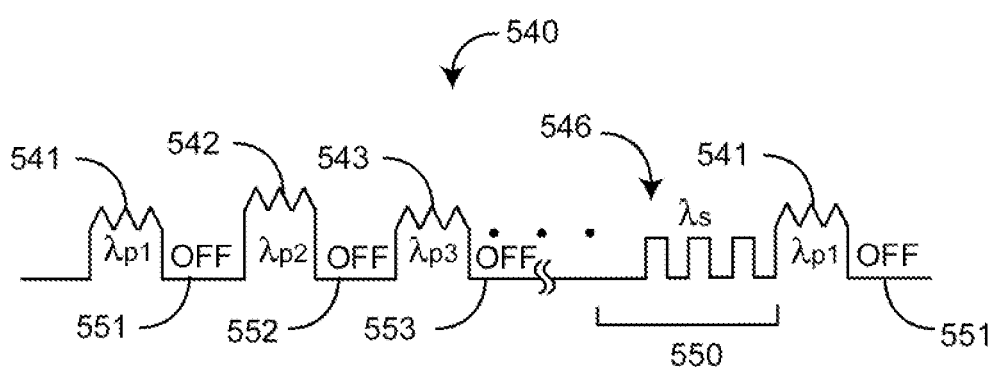

FIGS. 5A-C illustrate time diagrams for an emitter drive signal 500 and corresponding detector signals 520, 540 with synchronous and asynchronous secondary emitters, respectively. These emitter drive 500 and detector signals 520, 540 correspond to a sensor utilizing an internal or external secondary emitter, such as described with respect to FIGS. 4A-C, above. As shown in FIG. 5A, during primary emitter enable periods 501-503, drive current is supplied from monitor drivers 134 (FIG. 2) to selected primary emitters in sequence, causing the selected emitters to turn on and emit optical energy at a particular wavelength. During OFF periods 511-513, no drive current is supplied to any emitter, allowing demodulation of the detector signal. Detector signal demodulation is described in U.S. Pat. No. 5,919,134 entitled "Method and Apparatus for Demodulating Signals in a Pulse Oximetry System," which is assigned to Masimo Corporation, Irvine, Calif. and incorporated by reference herein.

Also shown in FIG. 5A, the drive signal 500 represents emitter drive currents activated and deactivated to various emitters. Included are emitter currents 501-503 for activating primary emitters 112 (FIG. 2) that transmit light having multiple wavelengths $\lambda_{p1}, \lambda_{p2}, \ldots \lambda_{pn}$ into a tissue site 10 (FIG. 2). Also included are emitter currents 506 for synchronously activating one or more secondary emitters having one or more wavelengths during an inactive period 510 for the primary emitters. For example, a single internal secondary emitter 116 (FIG. 2) of wavelength $\lambda_s$ may be activated after the primary emitters 112 (FIG. 2) have each be activated in sequence and before the start of another primary activation sequence, as shown. In another embodiment, there are no synchronous emitter currents 506 for activating secondary emitters. Rather, secondary emitters, either internal or external are free-running or are otherwise activated asynchronously from the primary drive currents, as described with respect to FIG. 5C, below.

As shown in FIG. 5B, a detector signal 520 represent detector current 152 (FIG. 2) in response to the emitter transmitted light after absorption by pulsatile bloodflow within the tissue 10 (FIG. 2). In particular, the detector signal 520 has response periods 521-523 corresponding to the primary emitter enable periods 501-503 (FIG. 5A) and off periods 531-533 corresponding to the primary emitter off periods 511-513 (FIG. 5A). Advantageously the detector signal 520 may also have one or more secondary emitter response intervals 530 that indicate a sensor-off condition. The DSP 138 (FIG. 2), for example, processes a secondary emitter response interval 530 so as to detect a synchronous secondary emitter response 526, which indicates a sensor-off condition. Correspondingly, failure to detect a synchronous secondary emitter response 526 within the interval 530 when a secondary emitter is activated 506 (FIG. 5A) is indicative of a sensor-on condition.

As shown in FIG. 5C, a detector signal 540 also represents detector current 152 (FIG. 2) in response to the emitter transmitted light after absorption by pulsatile blood flow within the tissue 10 (FIG. 2), including response periods 541-543 corresponding to the primary emitter enable periods 501-503 (FIG. 5A) and off periods 551-553 corresponding to the primary emitter off periods 511-513 (FIG. 5A). Advantageously the detector signal 540 may also have one or more secondary emitter response intervals 550 used to detect an asynchronous secondary emitter response 546 indicative of a sensor-off condition. That is, the DSP 138 (FIG. 2), may process an interval 550 known to be outside of any primary emitter activation sequence so as to determine if there is a detector response to an asynchronous secondary emitter, such as a free-running external emitter. Detection of a known secondary emitter activation sequence within the interval 550 is indicative of a sensor-off condition, and failure to detect such a sequence may be indicative of a sensor-on condition. As described above, the secondary emitter response intervals 530, 550 may include one or more on/off cycles of one or more synchronously or asynchronously activated secondary emitters.

Figure 6A:
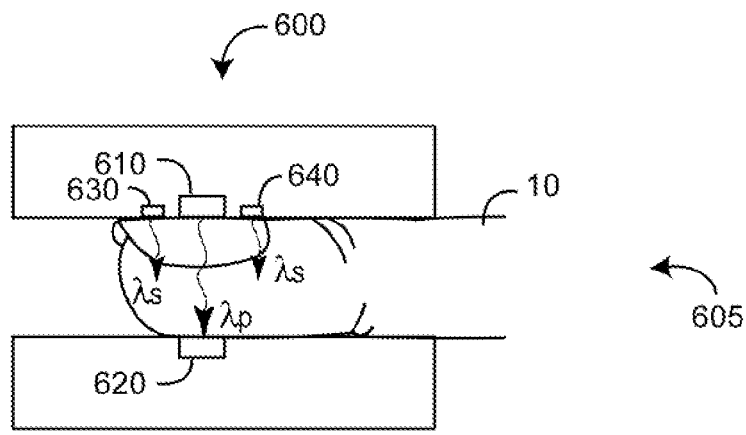
FIGS. 6A-C are side view illustrations of a secondary-emitter sensor position indicator illustrating sensor-on, sensor mis-positioned and sensor-off conditions, respectively.
Figure 6B:
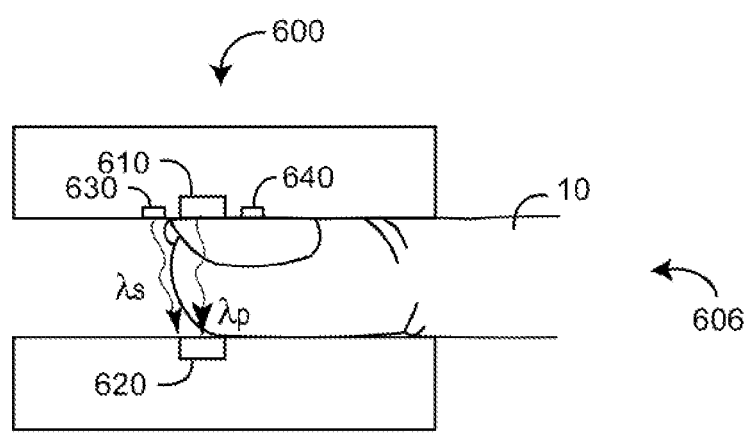
Figure 6C:
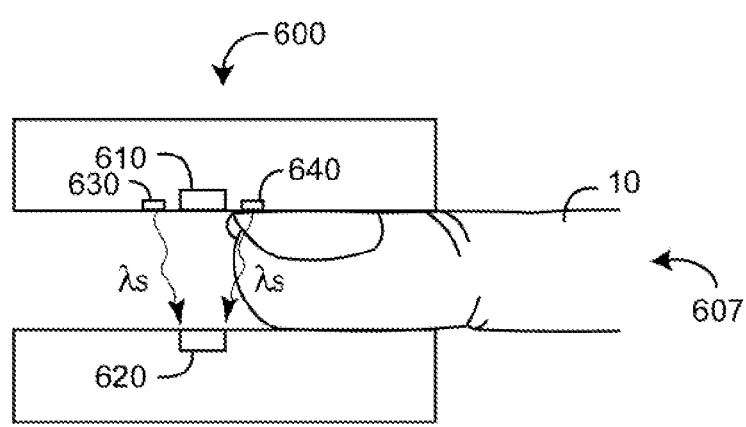

FIGS. 6A-C illustrate a multiple secondary-emitter sensor 600 advantageously configured to indicate multiple improper sensor placement conditions. In particular, the multiple secondary-emitter sensor 600 has a sensor-on condition 605, a sensor mis-positioned condition 606 and a sensor-off condition 607. The sensor 600 has a primary emitter 610 that emits light having multiple primary wavelengths $\lambda_p$ into a tissue site 10 and a detector 620 that detects the emitted light after attenuation by the tissue site 10. In the embodiment shown, the sensor 600 has two secondary emitters 630, 640 that emit light having a secondary wavelength $\lambda_s$ and that are placed relative to the primary emitter 610 so as to indicate the two improper placement sensor conditions.

As shown in FIG. 6A, in the sensor-on condition 605, tissue completely covers the detector 620 so that the detector 620 is not responsive to secondary emitters 630-640 of wavelength $\lambda_s$. As shown in FIG. 6B, in the sensor mis-positioned condition 606, the detector 620 is exposed to at least one secondary emitter 630 and is blocked by tissue from at least one secondary emitter 640. As shown in FIG. 6C, in the sensor-off condition 607, the detector 620 is exposed to light transmitted from multiple secondary emitters 630-640. Advantageously, a sensor mis-positioned condition 606 is differentially indicated from a sensor-off position 607 so that an attached monitor can more accurately inform a healthcare professional or monitor operator of an appropriate corrective action.

Although a multiple secondary-emitter sensor 600 is described above with two secondary emitters 630, 640 placed proximate to and on either side of the primary emitter 610, in other embodiments there may be more than two secondary-emitters. In other embodiments, the secondary emitters may both be located on the same side of the primary emitter, the secondary emitters may be placed at various locations around the primary emitter, the secondary emitters may be co-located within the primary emitter package or the secondary emitters may be placed at various combinations of the above-described sensor locations. Further, some or all of the secondary emitters may have the same or similar wavelengths $\lambda_s$ or some or all of the secondary emitters may have distinct wavelengths $\lambda_{s_1}, \lambda_{s_2}, \ldots \lambda_{s_n}$.

Figure 7A:
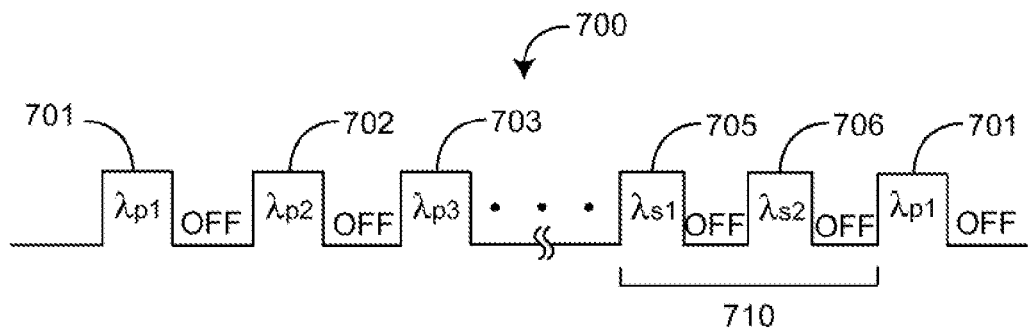
FIGS. 7A-D are timing diagrams for a secondary-emitter sensor position indicator illustrating primary and secondary emitter drive signals and corresponding detector output signals for sensor-on, sensor mis-positioned and sensor-off conditions.

FIGS. 7A-D illustrate sensor timing diagrams corresponding to a sensor having multiple secondary emitters, such as described with respect to FIGS. 6A-C, above. As shown in FIG. 7A, emitter drive signals 700 include activated and deactivated drive currents to multiple primary emitters 701-703 and multiple secondary emitters 705-706. In particular, during a secondary emitter activation interval 710, secondary emitters 630, 640 (FIGS. 6A-C) are activated 705, 706 in sequence with intervening OFF periods.

Figure 7B:
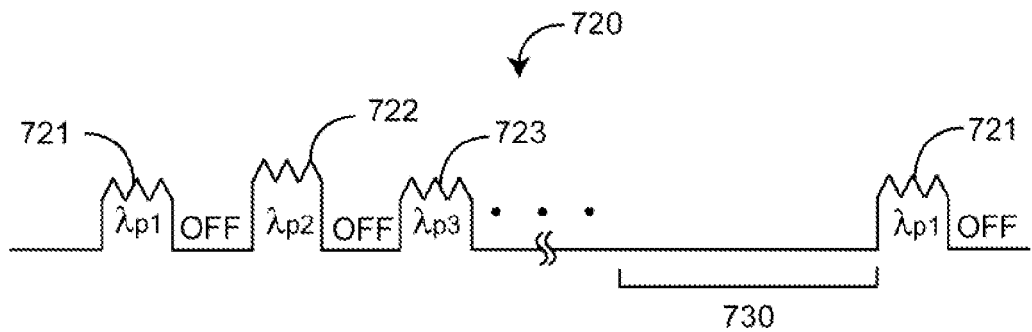
Figure 7C:
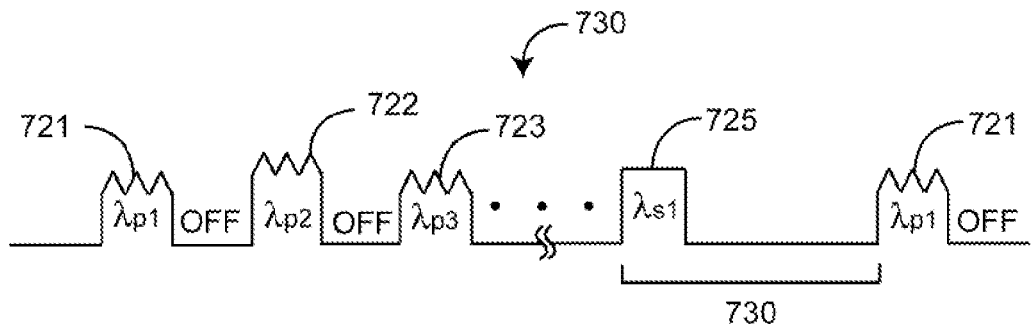
Figure 7D:
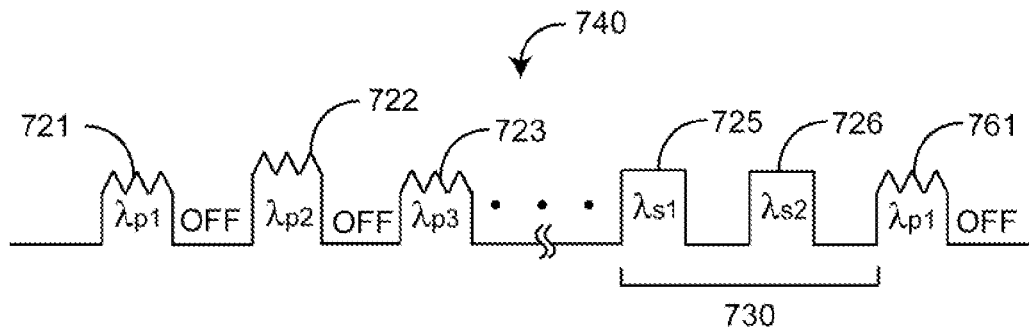

As shown in FIGS. 7B-D, a detector signal 720 corresponding to the emitter drive signals 700 is generated by the detector 114 (FIG. 2) and transmitted to the monitor 130 (FIG. 2) as a detector current 152 (FIG. 2). As shown in FIG. 7B, in a sensor-on condition 605 (FIG. 6A), light transmitted from the secondary emitters 630, 640 (FIG. 6A) is at least substantially absorbed by tissue 10 (FIG. 6A) properly placed between the emitters and the detector 620 (FIG. 6A). Hence, there is no detector current corresponding to secondary emitter activation during the activation interval 730 (FIG. 7B). Thus, the monitor 130 (FIGS. 1-2) can determine that there is proper placement of the sensor 110 (FIGS. 1-2).

As shown in FIG. 7C, in a mis-positioned sensor condition 606 (FIG. 6B), light transmission from at least one secondary emitter 630 (FIG. 6B) is not at least substantially absorbed by tissue, because the tissue site 10 (FIG. 6B) is not properly placed between the emitters 630, 640 (FIG. 6B) and the detector 620 (FIG. 6B). Hence, there is detector current 725 corresponding to a secondary emitter drive current 705 (FIG. 7A) during the activation interval 730. Thus, the monitor 130 (FIGS. 1-2) can determine that the sensor 110 (FIGS. 1-2) is mis-positioned.

As shown in FIG. 7D, in a sensor-off condition 607 (FIG. 6C), light transmission from all secondary emitters 630, 640 (FIG. 6C) is not at least substantially absorbed by tissue, as the sensor is substantially misplaced on the tissue site or is completely off of the tissue site 10 (FIG. 6C). Hence, there is detector current 725-726 corresponding to each secondary emitter drive current 705, 706 (FIG. 7A) during the activation interval 730. Thus, the monitor 130 (FIGS. 1-2) can determine that the sensor 110 (FIGS. 1-2) is substantially or completely off of the tissue site.

FIGS. 8A-D illustrate a secondary emitter/detector sensor 800 having secondary emitters and a secondary detector advantageously configured to indicate a sensor on condition and multiple improper sensor conditions. In particular, the secondary emitter/detector sensor 800 has a sensor-on condition 805, an over-positioned sensor condition 806, a sensor mis-positioned condition 807, and a sensor-off condition 808. In an over-positioned sensor condition 806, the sensor 800 indicates that the tissue site is inserted too far into the sensor. An over-positioned sensor condition 806 may occur, for example, in a removable finger clip sensor where a fingertip is over inserted, such as when a finger nail or other finger structure bypasses a blocking structure or indent.

The secondary emitter/detector sensor 800 has a primary emitter 810 that emits light having multiple primary wavelengths $\lambda p$ into a tissue site 10 and a primary detector 820 that detects the emitted light after attenuation by the tissue site 10. In the embodiment shown, the sensor 800 also has three secondary emitters 830-840 that emit light having a secondary wavelength $\lambda s$, which are placed relative to the primary emitter 810 so as to indicate the three improper placement sensor conditions.

Figure 8A:
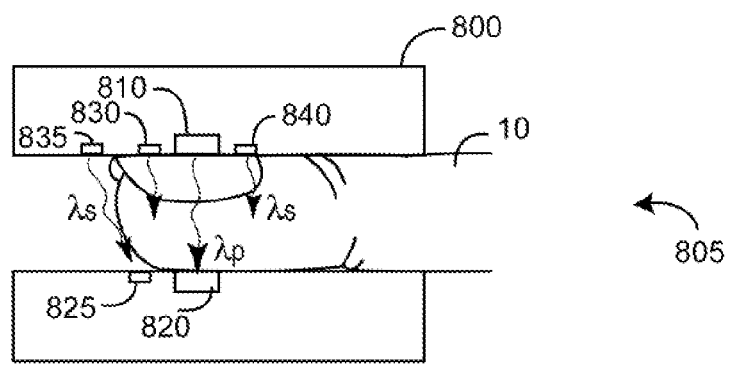
FIGS. 8A-D are side view illustrations of a secondary-emitter sensor position indicator illustrating sensor-on, sensor over-positioned, sensor mis-positioned and sensor-off conditions, respectively.

As shown in FIG. 8A, in the sensor-on condition 805, tissue completely covers the detector 820 so that the primary detector 820 is not responsive to secondary emitters 830-840. The secondary detector 825, however, is responsive to a secondary emitter 835 placed distal the primary emitter 810.

Figure 8B:
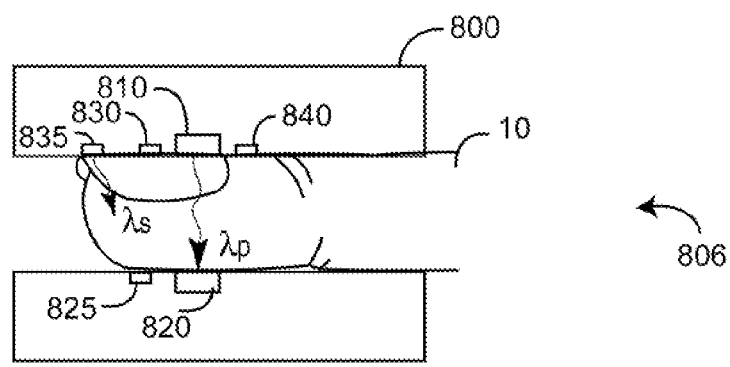

As shown in FIG. 8B, in the sensor over-positioned condition 806, the secondary detector 825 is not responsive to the secondary emitter 835. That is, light transmission from the secondary emitter 835 is at least substantially absorbed when tissue is over inserted between a secondary emitter 835 and secondary detector 825.

Figure 8C:
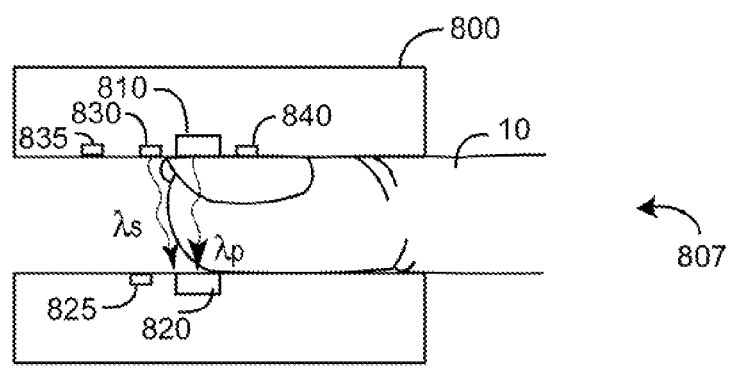
Figure 8D:
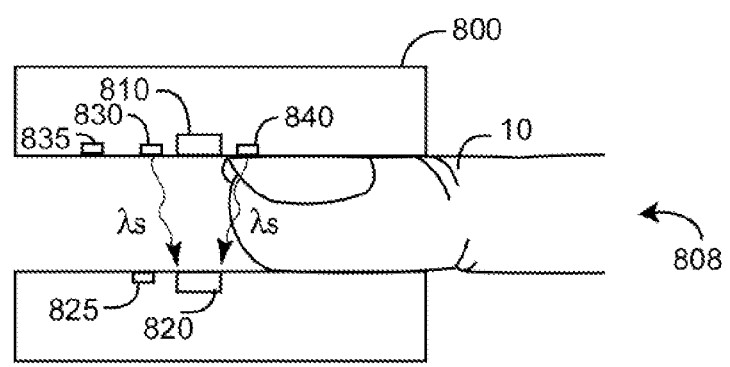

As shown in FIG. 8C, in the sensor mis-positioned condition 807, the detector 820 is exposed to at least one secondary emitter 830 and is blocked by tissue from at least one secondary emitter 840. As shown in FIG. 8D, in the sensor-off condition 808, the detector 620 is exposed to light transmitted from multiple secondary emitters 630-640. Advantageously, the various improperly placed sensor conditions 806-808 are differentially indicated from each other so that an attached monitor can more accurately inform a healthcare professional or monitor operator of an appropriate corrective action.

Figure 9A:
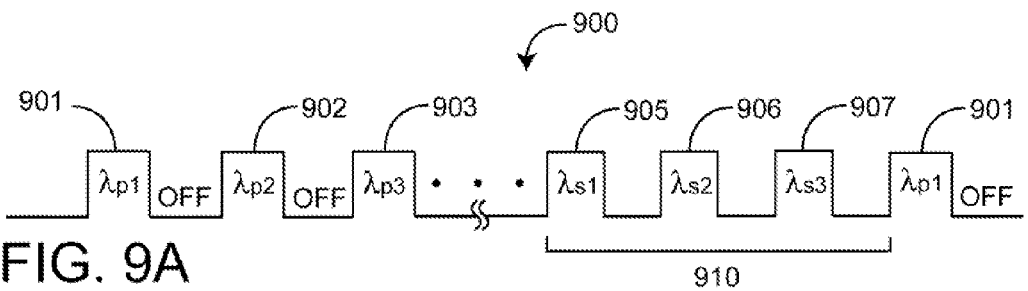
FIGS. 9A-E are timing diagrams for a secondary-emitter sensor position indicator illustrating primary and secondary emitter drive signals and corresponding detector output signals for sensor-on, sensor over-positioned, sensor mis-positioned and sensor-off conditions, respectively.

FIGS. 9A-E illustrate sensor timing diagrams corresponding to a secondary emitter/detector sensor 800 (FIGS. 8A-D), such as described above. These timing diagrams including input emitter drive signals 900 and corresponding combined primary and secondary detector output signals 950-980 indicating a sensor-on condition and various improper sensor position conditions. As shown in FIG. 9A, emitter drive signals 900 include drive currents activated and deactivated to multiple primary emitters 901-903 and multiple secondary emitters 905-907 during a secondary emitter activation interval 910.

Figure 9B:
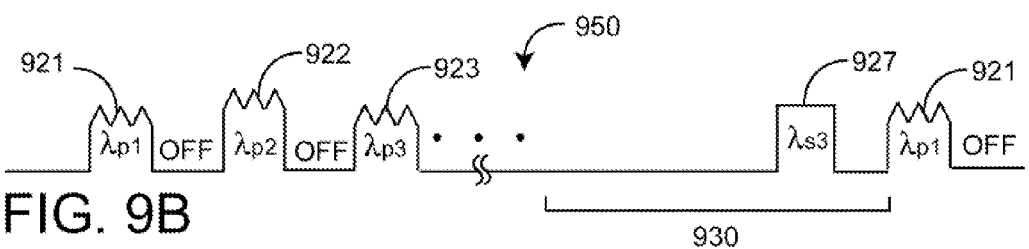

As shown in FIG. 9B, in a sensor-on condition 805 (FIG. 8A), a primary detector response current 921-923 is generated by the primary detector 820 (FIG. 8A) in response to light received during emitter activation 901-903. Also, a secondary detector response current 927 is generated by the secondary detector 825 (FIG. 8A) in response to light received during a secondary response interval 930 in response to secondary emitter activation 907.

Figure 9C:
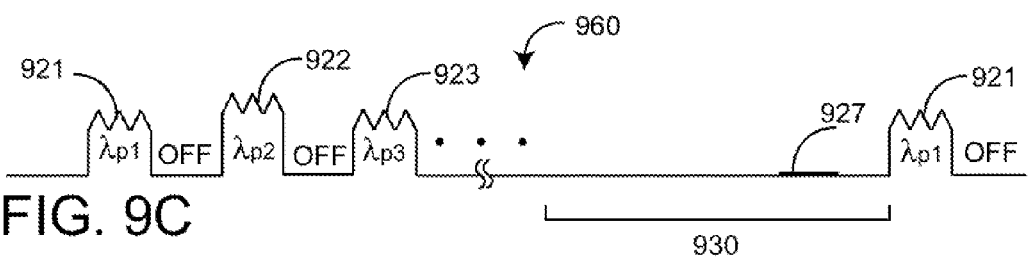

As shown in FIG. 9C, in a sensor over-positioned condition 806 (FIG. 8A), a primary detector response current 921-923 is generated by the primary detector 820 (FIG. 8A) as described with respect to FIG. 9B, above. However, the secondary detector response current 927 for a sensor over-position condition is substantially null during the secondary activation interval 930 as light transmission at wavelength $\lambda s$ is at least substantially absorbed by the tissue over-inserted between the detector and the secondary emitter 825, 835 (FIG. 8B).

Figure 9D:
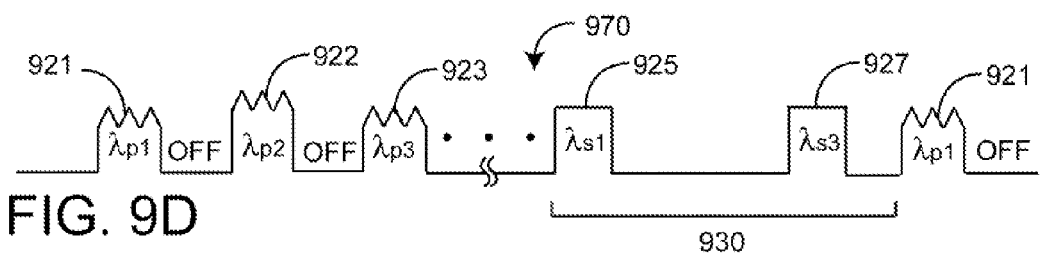

As shown in FIG. 9D, in a mis-positioned sensor condition 807 (FIG. 8C) light transmission from at least one secondary emitter 830 (FIG. 8C) is not at least substantially absorbed by tissue, which is not properly placed between the secondary emitters 830, 840 (FIG. 8C) and the primary detector 820 (FIG. 8C). Hence, there is primary detector current 925 corresponding to a secondary emitter drive current 905 (FIG. 9A) during the activation interval 930. Thus, the monitor 130 (FIGS. 1-2) can determine that the sensor is mis-positioned.

Figure 9E:
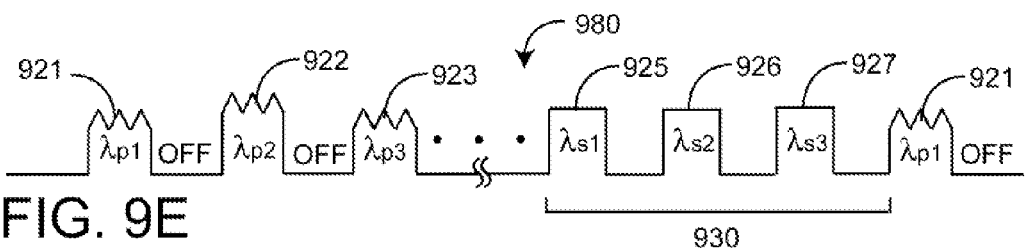

As shown in FIG. 9E, in a sensor off condition 808 (FIG. 8D) light transmission from all secondary emitters 830 is not at least substantially absorbed by tissue, which is either substantially misplaced between the secondary emitters 830, 840 (FIG. 8D) and the primary detector 820 (FIG. 8D) or the sensor is entirely off of the tissue site. Hence, there is detector current 925-927 corresponding to secondary emitter drive current 905-907 (FIG. 9A) during the activation interval 930. Note that primary detector current 921-923 in response to primary emitter drive current 901-903 may have an AC component that appears normal, i.e. due to pulsatile blood absorption, despite the absence of tissue, as described in the summary, above.

A secondary-emitter sensor position indicator has been disclosed in detail in connection with various embodiments. These embodiments are disclosed by way of examples only and are not to limit the scope of the claims that follow. One of ordinary skill in art will appreciate many variations and modifications.

What is claimed is:

1. A sensor position indicator having an optical sensor with a sensor-on condition in which the optical sensor is attached to and aligned with a tissue site so as to transmit light into the tissue site and detect the light after attenuation by pulsatile blood flow within the tissue site and a sensor out-of-position condition in which the sensor is unattached to or misaligned with the tissue site, the sensor position indicator comprising:
   an optical sensor having a plurality of primary emitters and a detector;
   the primary emitters generating light generally centered around each of a plurality of primary wavelengths;
   the primary emitters transmitting light into a tissue site in a sensor-on condition;
   the detector, in the sensor-on condition, outputting a sensor signal responsive to the primary wavelength light after attenuation by pulsatile blood flow within the tissue site;
   a secondary emitter that generates light generally centered around a secondary wavelength;
   the secondary emitter transmitted light is at least substantially attenuated by the tissue site;
   the detector, in the sensor-on condition, is at least substantially blocked by the tissue site from the secondary emitter so that the sensor signal is not responsive to the secondary wavelength light;
   the detector, in a sensor out-of-position condition, is at least partially exposed to the secondary emitter so that the sensor signal is responsive to the secondary wavelength light; and
   a processor responsive to the sensor signal so as to calculate a blood-related physiological parameter in the sensor-on condition and so as to indicate the sensor is unattached to or misaligned with the tissue site in the sensor out-of-position condition;
   wherein the secondary emitter is driven asynchronously relative to the primary emitters.

2. The sensor position indicator according to claim 1 wherein the optical sensor has a sensor mis-positioned condition in which the optical sensor is misaligned with the tissue site, the sensor position indicator further comprising:
   a second secondary emitter that generates light generally centered around the secondary wavelength;
   the detector, in the sensor mis-positioned condition, is at least substantially blocked from the second secondary emitter by the tissue site and is at least partially exposed to the secondary emitter so that the sensor signal is not responsive to the second secondary emitter and is responsive to the secondary emitter, and
   the processor is responsive to the sensor signal so as to indicate the optical sensor is misaligned with the tissue site in the mis-positioned sensor condition.

3. The sensor position indicator according to claim 2 wherein the optical sensor has a sensor-off position in which the optical sensor is unattached to or substantially misplaced on the tissue site:
   the detector, in the sensor-off condition, is at least partially exposed to the secondary emitter and the second secondary emitter so that the sensor signal is responsive to both the secondary emitter and the second secondary emitter, and
   the processor is responsive to the sensor signal so as to indicate that the optical sensor is unattached to or substantially misplaced on the tissue site in the sensor-off condition.

4. The sensor position indicator according to claim 3 wherein the optical sensor has a sensor over-positioned condition where the tissue site is over-inserted into the optical sensor, the sensor position indicator further comprising:
   a third secondary emitter that generates light generally centered around the secondary wavelength;
   the detector, in the sensor-on condition, is at least substantially exposed to the third secondary emitter so that the sensor signal is responsive to the third secondary emitter;
   the detector, in the sensor over-positioned condition, is at least substantially blocked from the third secondary emitter by the tissue site so that the sensor signal is not responsive to the third secondary emitter;
   the processor is responsive to the sensor signal so as to indicate the tissue site is over-inserted into the optical sensor in the sensor over-positioned condition.

5. The sensor position indicator according to claim 4 wherein the primary wavelengths include red and IR and the secondary wavelength is at least one of blue and green.

6. A sensor position indicator having an optical sensor with a sensor-on condition in which the optical sensor is attached to and aligned with a tissue site so as to transmit light into the tissue site and detect the light after attenuation by pulsatile blood flow within the tissue site and a sensor out-of-position condition in which the sensor is unattached to or misaligned with the tissue site, the sensor position indicator comprising:
   an optical sensor having a plurality of primary emitters and a detector;
   the primary emitters generating light generally centered around each of a plurality of primary wavelengths;
   the primary emitters transmitting light into a tissue site in a sensor-on condition;
   the detector, in the sensor-on condition, outputting a sensor signal responsive to the primary wavelength light after attenuation by pulsatile blood flow within the tissue site;
   a secondary emitter that generates light generally centered around a secondary wavelength;

the secondary emitter transmitted light is at least substantially attenuated by the tissue site;

the detector, in the sensor-on condition, is at least substantially blocked by the tissue site from the secondary emitter so that the sensor signal is not responsive to the secondary wavelength light;

the detector, in a sensor out-of-position condition, is at least partially exposed to the secondary emitter so that the sensor signal is responsive to the secondary wavelength light; and a processor responsive to the sensor signal so as to calculate a blood-related physiological parameter in the sensor-on condition and so as to indicate the sensor is unattached to or misaligned with the tissue site in the sensor out-of-position condition;

wherein the secondary emitter is located external to the optical sensor so that the secondary wavelength light is ambient light with respect to the optical sensor.

7. An optical sensing method comprising:

providing an optical sensor having a primary emitter and a detector;

activating the primary emitter with a primary drive signal so as to transmit light having a primary wavelength into a fleshy tissue site;

activating a secondary emitter with a secondary drive signal so as to transmit light having a secondary wavelength proximate the fleshy tissue site;

detecting the primary wavelength light after attenuation by pulsatile blood flow within the tissue site;

detecting the secondary wavelength light;

calculating a physiological parameter according to detected primary wavelength light;

determining a sensor position of the primary emitter and the detector relative to the fleshy tissue site according to the detection of secondary wavelength light; and synchronizing the primary drive signal and the secondary drive signal so that on periods of the secondary drive signal occur during off periods of the primary drive signal.

8. The optical sensing method according to claim 7 wherein the determining comprises:

indicating a sensor-on condition according to undetected secondary wavelength light during an on period of the secondary drive signal; and indicating a sensor out-of-position condition according to undetected secondary wavelength light during on periods of the secondary drive signal.

9. The optical sensing method according to claim 8 further comprising:

activating a second secondary emitter with a second secondary drive signal; and indicating a sensor-off condition according to the undetected secondary wavelength light during on periods of the secondary drive signal and second secondary drive signal.

10. The optical sensing method according to claim 9 further comprising:

indicating a sensor mis-position condition according to detected secondary wavelength light during on periods of the secondary drive signal and according to undetected secondary wavelength light during on periods of the second secondary drive signal.

11. The optical sensing method according to claim 10 further comprising:

activating a third secondary emitter with a third secondary drive signal; and indicating a sensor over-position condition according to detected secondary wavelength light during on periods of the third secondary drive signal.

12. A physiological measurement system comprising:

an optical sensor having a plurality of primary emitters, at least one secondary emitter, a detector and an attachment assembly;

a physiological monitor in communications with the optical sensor;

the primary emitters transmit light having a plurality of primary wavelengths;

the at least one secondary emitter transmits light having at least one secondary wavelength;

the detector outputs a sensor signal in response to received light;

the attachment assembly, in a sensor-on condition, positions the emitters and detector relative to a tissue site so that the sensor signal is substantially responsive to the primary wavelength light after attenuation by pulsatile blood flow within the tissue site and is negligibly responsive to the secondary wavelength light, and the attachment assembly, in a sensor out-of-position condition, positions the at least one secondary emitter relative to the tissue site so that the sensor signal is at least partially responsive to the at least one secondary wavelength;

wherein the secondary emitter is driven asynchronously relative to the primary emitters.

13. The physiological measurement system according to claim 12 further comprising:

a first secondary emitter located in a first position relative to the primary emitters;

a second secondary emitter located in a second position relative to the primary emitters; and the attachment assembly, in a sensor mis-positioned condition, positions the secondary emitters relative to the tissue site so that the sensor signal is negligibly responsive to the first secondary emitter and at least partially responsive to the second secondary emitter.

14. The physiological measurement system according to claim 13 wherein the attachment assembly, in a sensor-off condition, positions the secondary emitters relative to the tissue site so that the sensor signal is at least partially responsive to the first secondary emitter and the second secondary emitter.

15. The physiological measurement system according to claim 14 further comprising:

a third secondary emitter located in a third position relative to the primary emitters;

the attachment assembly, in a sensor-on condition, positions the secondary emitters relative to the tissue site so that the sensor signal is negligibly responsive to the first and second secondary emitters and at least partially responsive to the third secondary emitter; and the attachment assembly, in a sensor over-positioned condition, positions the secondary emitters relative to the tissue site so that the sensor signal is negligibly responsive to the first, second and third secondary emitters.

16. The physiological measurement system according to claim 15 further comprising:

a processor portion of the physiological monitor; and the processor operating on the sensor signal so as to determine the position of a finger relative to the sensor according to at least multiple ones of a sensor-on condition, a sensor out-of-position condition, a sensor off condition and a sensor mis-positioned condition.

17. The physiological measurement system according to claim 16 further comprising:
a display portion of the physiological monitor; and
the display responsive to the processor determination of sensor and finger position so as to graphically depict the position of a finger relative to the sensor.

18. The physiological measurement system according to claim 17 further comprising:
an alarm portion of the physiological monitor; and
the alarm responsive to the processor determination of sensor and finger position so as to audibly indicate the position of a finger relative to the sensor.

\* \* \* \* \*

UNITED STATES PATENT AND TRADEMARK OFFICE
CERTIFICATE OF CORRECTION

PATENT NO.       : 8,401,602 B2
APPLICATION NO.  : 12/577667
DATED            : March 19, 2013
INVENTOR(S)      : Massi Joe E. Kiani It is certified that error appears in the above-identified patent and that said Letters Patent is hereby corrected as shown below:

Title Page

On Page 2 (Item 56), Column 2, Line 17, under U.S. Patent Documents, change "Al-All" to --Al-Ali--.

Specification

In Column 1, Line 58, change "Rad57™" to --Rad-57™--.

In Column 1, Line 58, change "Rad87™" to --Rad-87™--.

In Column 8, Line 3, change "$\lambda_s$" to --$\lambda s$--.

In Column 8, Line 56, change "$\lambda_p$" to --$\lambda p$--.

In Column 8, Line 66, change "$\lambda_s$." to --$\lambda s$.--.

In Column 9, Line 20, change "$\lambda_s$" to --$\lambda s$--.

Signed and Sealed this
Nineteenth Day of January, 2016

Michelle K. Lee
*Director of the United States Patent and Trademark Office*